US010525435B2

(12) United States Patent
Franci et al.

(10) Patent No.: US 10,525,435 B2
(45) Date of Patent: Jan. 7, 2020

(54) PIERCING DEVICE

(71) Applicant: GE Healthcare Limited, Buckinghamshire (GB)

(72) Inventors: Xavier Franci, Loncin (BE); Philippe Dumont, Loncin (BE); Steve Lignon, Loncin (BE); Audrey Marie Lange, Loncin (BE); Nicolas Verbrugge, Loncin (BE)

(73) Assignee: GE HEALTHCARE LIMITED, Buckinghamshire (GB)

( * ) Notice: Subject to any disclaimer, the term of this patent is extended or adjusted under 35 U.S.C. 154(b) by 193 days.

(21) Appl. No.: 15/546,924

(22) PCT Filed: Mar. 10, 2016

(86) PCT No.: PCT/EP2016/055178
§ 371 (c)(1),
(2) Date: Jul. 27, 2017

(87) PCT Pub. No.: WO2016/146482
PCT Pub. Date: Sep. 22, 2016

(65) Prior Publication Data
US 2018/0008949 A1 Jan. 11, 2018

(30) Foreign Application Priority Data
Mar. 13, 2015 (GB) .................................. 1504287.2

(51) Int. Cl.
*B01J 19/00* (2006.01)
*A61K 51/04* (2006.01)
(Continued)

(52) U.S. Cl.
CPC ......... *B01J 19/004* (2013.01); *A61K 51/0491* (2013.01); *B01J 19/18* (2013.01); *C07H 5/02* (2013.01); *C07B 2200/05* (2013.01)

(58) Field of Classification Search
CPC ...... B01J 19/004; B01J 19/00; B01J 19/0093; A61K 51/0491; A61K 51/04; A61K 51/00
(Continued)

(56) References Cited

U.S. PATENT DOCUMENTS

2008/0233653 A1    9/2008  Hess et al.
2011/0006011 A1*   1/2011  Aerts ..................... A61K 51/04
                                                           210/682
(Continued)

FOREIGN PATENT DOCUMENTS

CN    103827975 A    5/2014
EP    1216715 A1    6/2002
(Continued)

OTHER PUBLICATIONS

International Search Report and the Written Opinion of the International Searching Authority, or the Declaration from International Appl. No. PCT/EP2016/055178, dated Jun. 15, 2016.
(Continued)

*Primary Examiner* — Christine T Mui
(74) *Attorney, Agent, or Firm* — Arent Fox, LLP

(57) ABSTRACT

The present invention provides a system for the production of a radiopharmaceutical including a radiosynthesis apparatus and a disposable cassette. The system of the invention includes a device that enables a position on the cassette to be freed for inclusion of an additional reagent vial. With the system of the invention a broader range of radiochemical syntheses can be envisaged using the cassette.

11 Claims, 5 Drawing Sheets

(51) Int. Cl.
   *B01J 19/18* (2006.01)
   *C07H 5/02* (2006.01)
   *A61K 51/00* (2006.01)

(58) Field of Classification Search
   USPC .......................................... 422/502, 500, 50
   See application file for complete search history.

(56) References Cited

U.S. PATENT DOCUMENTS

2013/0334443 A1* 12/2013 Steel ..................... B65B 3/003
                                                              250/506.1
2014/0229152 A1*  8/2014 Chisholm ............. B01J 19/004
                                                              703/13

FOREIGN PATENT DOCUMENTS

| JP | H10148628 A | 6/1998 |
|---|---|---|
| WO | 2010021719 A1 | 2/2010 |
| WO | 2013048813 A1 | 4/2013 |
| WO | 2013049608 A2 | 4/2013 |
| WO | 2013049806 A1 | 4/2013 |
| WO | 2015071288 A1 | 5/2015 |
| WO | 2016146482 A1 | 9/2016 |

OTHER PUBLICATIONS

Great Britain Search Report from GB Appl. No. GB1504287.2, dated Dec. 17, 2015.

Mark Lazari et al., "ELIXYS—A Fully Automated, Three-Reactor High Pressure Radiosynthesizer for Development and Routine Production of Diverse PET Tracers," EJNMMI Research 2013, vol. 3(1), pp. 1-13.

China Office Action and Search Report corresponding to Chinese Application No. 201680015345.1, dated Apr. 16, 2019 and Apr. 8, 2019.

* cited by examiner

PIERCING DEVICE

TECHNICAL FIELD OF THE INVENTION

The present invention relates to the synthesis of radiolabelled compounds. In particular, the present invention relates to methods for the automated synthesis of radiolabelled compounds, especially where those compounds are suitable for use in radiopharmaceutical preparations.

DESCRIPTION OF RELATED ART

Radiolabelled compounds for use as in vivo imaging agents are currently typically prepared by means of an automated synthesis apparatus (alternatively "radiosynthesizer"). Such automated synthesis apparatuses are commercially available from a range of suppliers, including: GE Healthcare; CTI Inc.; Ion Beam Applications S.A. (Chemin du Cyclotron 3, B-1348 Louvain-La-Neuve, Belgium); Raytest (Germany) and Bioscan (USA). The radiochemistry takes place in a "cassette" or "cartridge" designed to fit removably and interchangeably onto the apparatus, in such a way that mechanical movement of moving parts of the apparatus controls the operation of the cassette. Suitable cassettes may be provided as a kit of parts that is assembled onto the apparatus in a number of steps, or may be provided as a single piece that is attached in a single step, thereby reducing the risk of human error. The single piece arrangement is generally a disposable single use cassette which comprises all the reagents, reaction vessels and apparatus necessary to carry out the preparation of a given batch of radiopharmaceutical.

The commercially-available GE Healthcare FASTlab™ cassette is an example of a disposable single piece type of cassette pre-loaded with reagents comprising a linear array of valves, each linked to a port where reagents or vials can be attached. Each valve has a male-female joint which interfaces with a corresponding moving arm of the automated synthesis apparatus. External rotation of the arm thus controls the opening or closing of the valve when the cassette is attached to the apparatus. Additional moving parts of the apparatus are designed to clip onto syringe plunger tips, and thus raise or depress syringe barrels. The FASTlab™ cassette has 25 identical 3-way valves in a linear array, including reagent locations were spikes allow to connect the reagent vials to the cassette manifold. There are 2 fixed reagent barrels for 11 mm vials and 4 fixed reagent barrels for 13 mm vials, respectively in position 2, 12, 13, 14, 15 and 16. Position 15 is allocated to the water bag spike because it is linked to a water bottle holder located above the position 15. The known FASTlab™ cassette configuration has 5 fixed locations available for reagent vials. However, for some radiochemical processes there is a need for more than 5 reagent vials. Further, where it is desired to produce multiple batches of a radiopharmaceutical from one cassette additional capacity is required.

SUMMARY OF THE INVENTION

The present invention provides a system for the production of a radiopharmaceutical comprising:
(i) a cassette (2) comprising all the reagents required to produce two batches of said radiopharmaceutical when a radioisotope is introduced into said cassette (2), wherein each of said reagents is contained in a stoppered reagent vial (3a-g) that is pierced by a spike (4a-g) by automated movement of said stoppered reagent vial (3a-g) and/or said spike (4a-g);
(ii) an automated radiosynthesiser (5) onto which said cassette removably fits and which comprises moving parts that control operation of the cassette (2), wherein one such moving part is a device (6) to facilitate the automated piercing of one of said stoppered reagent vials (3a-g) wherein said device (6) is attached to the outside of said automated radiosynthesiser (5) and comprises a support (7) and a substantially rigid rod (8) housed within said support (7).

The present invention also provides a device (6) as defined herein for the system of the invention.

The presence of the device in the system of the invention enables a position on the cassette to be adapted for inclusion of an additional reagent vial. Therefore with the system of the invention a broader range of radiochemical syntheses can be carried out compared with known cassettes.

DETAILED DESCRIPTION OF THE PREFERRED EMBODIMENTS

Figure 1:
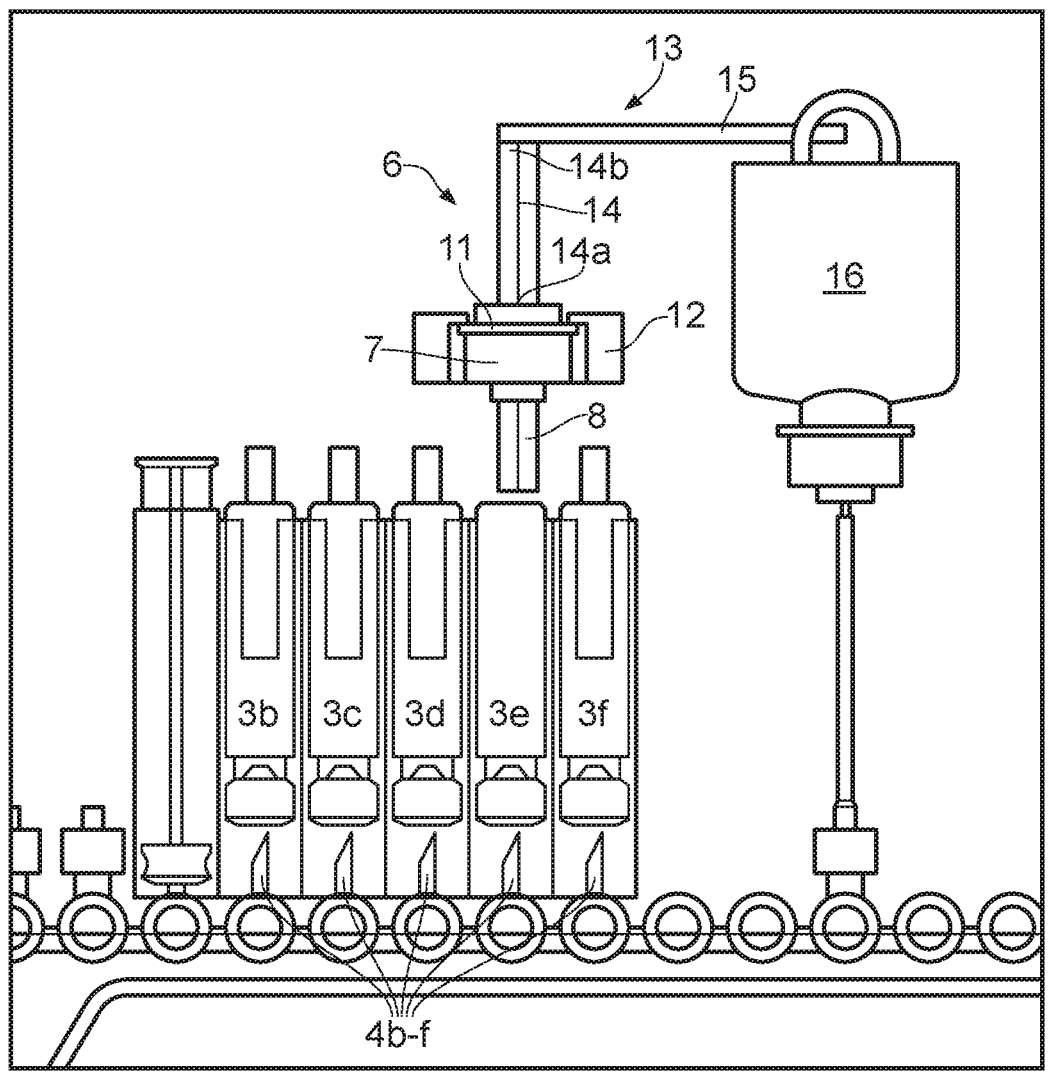
FIG. 1 illustrates a section of a FASTlab™ cassette wherein an exemplary device (6) of the present invention is used to enable insertion of an additional reagent vial (3e) at a position where in the existing FASTlab™ device a water bottle is accommodated.

To more clearly and concisely describe and point out the subject matter of the claimed invention, definitions are provided hereinbelow for specific terms used throughout the present specification and claims. Any exemplification of specific terms herein should be considered as a non-limiting example.

A "system for the production of a radiopharmaceutical" is an apparatus configured for the automated synthesis of a radiolabelled compound suitable for use as an in vivo diagnostic agent. The system is suitably manufactured from materials of pharmaceutical grade and resistant to radiolysis. The system should be designed with the aim of obtaining a radiopharmaceutical preparation that is suitable for mammalian administration, i.e. sterile, non-pyrogenic, and for use as an in vivo imaging agent, i.e. sufficient purity of the active pharmaceutical ingredient and retaining sufficient radioactivity to permit a clinically-useful image to be obtained. Those of skill in the art of preparing radiopharmaceuticals will be well-acquainted with these requirements. In this respect, the reader is referred e.g. to "Radiochemical Syntheses: Radiopharmaceuticals for Positron Emission Tomography" (Volume 1, 2001, Wiley, Scott & Hockley, Eds.) and to "Handbook of Radiopharmaceuticals: Radiochemistry and Applications" (2003, Wiley, Welch &

Redvanly, Eds.) for discussion of the common general knowledge in the art of radiopharmaceutical preparation.

The term "radiopharmaceutical" broadly speaking refers to a medicinal compound that has a radioactive component. Radiopharmaceuticals are used in the field of nuclear medicine as either radioactive tracers in medical imaging or in therapy e.g. radiotherapy, brachytherapy. Radiopharmaceuticals for medical imaging typically incorporate a radioactive isotope into a pharmaceutically-active molecule, which is localized in the body following administration. For medical imaging applications, the radioactive isotope allows the location of the radiopharmaceutical in the body to be easily detected with a gamma camera or similar imaging device, e.g. a single-photon emission tomography (SPECT) imaging device or a positron emission tomography (PET) imaging device.

By the term "cassette" as used herein refers to a piece of apparatus designed to fit removably and interchangeably onto an automated radiosynthesiser, in such a way that mechanical movement of moving parts of the radiosynthesiser controls the operation of the cassette from outside the cassette, i.e. externally. Exemplary cassettes comprise a linear array of valves, each linked to a port where reagents or vials can be attached, by either needle puncture of an inverted septum-sealed vial, or by gas-tight, marrying joints. In one embodiment each valve is a 3-way valve. In one embodiment each valve is a stopcock valve comprising a rotatable stopcock. Each valve has a male-female joint which interfaces with a corresponding moving arm of the automated synthesis apparatus. External rotation of the arm thus controls the opening or closing of the valve when the cassette is attached to the automated radiosynthesiser. Additional moving parts of the automated radiosynthesiser are designed to clip onto syringe plunger tips, and thus raise or depress syringe barrels. The cassette is versatile, typically having several positions where reagents can be attached, and several suitable for attachment of syringe vials of reagents or chromatography columns. The cassette typically comprises a reaction vessel, generally configured such that 3 or more ports of the cassette are connected thereto to permit transfer of reagents or solvents from various ports on the cassette. Cassettes need to be designed to be suitable for radiopharmaceutical manufacture and are therefore manufactured from materials which are of pharmaceutical grade as well as resistant to radiolysis. Those of skill in the art will be aware of the most suitable materials. The reader is referred to the common general knowledge in the art as described for example in Chapter 5 of "Clinical PET and PET/CT: Principles and Applications" ($2^{nd}$ Edition 2013; Springer: E. Edmund Kim et al., Eds.). In one embodiment of the present invention the single-use cassette is a FASTlab™ cassette, i.e. one which is suitable for use with a FASTlabυ automated radiosynthesiser.

The term "single-use" as used in the context of a cassette of the present invention means that the cassette is intended to be used once prior to disposal. This single use in one embodiment is for the production of multiple batches of a radiopharmaceutical. In one embodiment the single use is for the production of two batches of an $^{18}F$-labelled compound.

The term "reagents" as used herein refers to the reactants and solvents required to carry out a particular radiochemical synthesis.

The term "radioisotope" refers to any isotope of an element having an unstable nucleus that dissipates excess energy by spontaneously emitting radiation in the form of alpha, beta, and/or gamma rays. More specifically in the context of the present invention, the term encompasses radioisotopes that are suitable for use in nuclear medicine applications. Non-limiting examples of commonly used radioisotopes for nuclear medicine include technetium-99m, iodine-123 and 131, thallium-201, gallium-67, carbon-11, fluorine-18 and indium-111.

A "stoppered reagent vial" in the context of the present invention is suitably a clinical grade container which is provided with a seal suitable for single or multiple puncturing, such as with a hypodermic needle or a spike (e.g. a crimped-on septum seal closure) while maintaining sterile integrity. Suitable containers comprise a sealed vessel which permits maintenance of sterile integrity and/or radioactive safety, while permitting addition and withdrawal of solutions by syringe. A preferred such container is a septum-sealed vial, wherein the gas-tight closure is crimped on with an overseal (typically of a metal such as aluminium). Such containers have the additional advantage that the closure can withstand vacuum if desired e.g. to change the headspace gas or degas solutions.

The term "pierced" in connection with the stoppered reagent vial takes its ordinary meaning, i.e. the vial is pierced when a needle or spike has punctured the seal so that the contents of the vial can be accessed, i.e. the needle or spike, being hollow, creates a fluid pathway from the interior of the vial to another component of the system of the invention such as a reaction vessel present in the cassette.

The term "spike" as used herein refers to a hollow tube associated with a valve of the cassette and configured to pierce the stopper of a reagent vial without being broken and permitting a sealed fluid path to be created with the inside of the vial and another component of the cassette. The spike should be made from material robust enough not to break; one non-limiting example being a hard plastic material. The spike should also be sufficiently sharp at its piercing end to be able to penetrate the vial stopper with relative ease, e.g. in one embodiment the spike has a pointed end.

The term "automated movement" refers to a movement of any part of the system of the invention controlled without direct human intervention, i.e. by use of one or more of various means including mechanical, hydraulic, pneumatic, electrical, electronic and computer. In one embodiment automated movement is directed by instructions sent to mechanical parts from a computer running software instructions that direct the movement.

By the term "automated radiosynthesiser" is meant an automated module based on the principle of unit operations as described by Satyamurthy et al (1999 Clin Positr Imag; 2(5): 233-253). The term "unit operations" means that complex processes are reduced to a series of simple operations or reactions, which can be applied to a range of materials. Such automated radiosynthesisers are commercially available from a range of suppliers (Satyamurthy et al, above), including: GE Healthcare; CTI Inc; Ion Beam Applications S.A. (Chemin du Cyclotron 3, B-1348 Louvain-La-Neuve, Belgium); Raytest (Germany) and Bioscan (USA). Automated radiosynthesisers are designed to be employed in a suitably configured radioactive work cell, or "hot cell", which provides suitable radiation shielding to protect the operator from potential radiation dose, as well as ventilation to remove chemical and/or radioactive vapours. Using a cassette the automated radiosynthesiser has the flexibility to make a variety of different radiopharmaceuticals with minimal risk of cross-contamination, by simply changing the cassette. This approach also has the advantages of simplified set-up hence reduced risk of operator error, improved GMP (good manufacturing practice) compliance, multi-tracer capability, rapid change between production runs, pre-run automated diagnostic checking of the cassette and reagents, automated cross-check (e.g. using a barcode or radio-frequency identification) of chemical reagents vs the synthesis to be carried out, reagent traceability, single-use and hence no risk of cross-contamination, tamper and abuse resistance.

The term "removably fits" in the present invention refers to the fact that the cassette fits to the automated radiosynthesiser but can also be removed, i.e. in order for the used cassette to be disposed of and for a new cassette to be fitted.

The wording "moving parts that control operation of the cassette" include but are not limited to e.g. the moving arms for controlling the opening or closing of the valves, those moving parts designed to clip onto syringe plunger tips to raise or depress syringe barrels.

The wording "attached to the outside of said automated radiosynthesiser" used in connection with the device can be understood to mean that the support of the device is connected to the automated radiosynthesiser in such a way as it is securely connected but also permitting movement of the device towards (and away from) the reagent vial. Movement towards said reagent vial brings the rod of the device into contact with the non-stoppered end of the reagent vial and urges the reagent vial towards its respective spike on the cassette resulting in piercing of the stopper as described hereinabove.

The term "support" as used herein refers to that part of the device that is attached to the automated radiosynthesiser and that holds the rod of the device in place. Suitably, said support is made from a rigid material such as a rigid plastic.

The term "substantially rigid rod" refers to that part of the device housed within the support that functions to urge the reagent vial towards its respective stopper, as discussed hereinabove. Suitably, like said support, said rod is made from a rigid material such as a rigid plastic.

Figure 5:
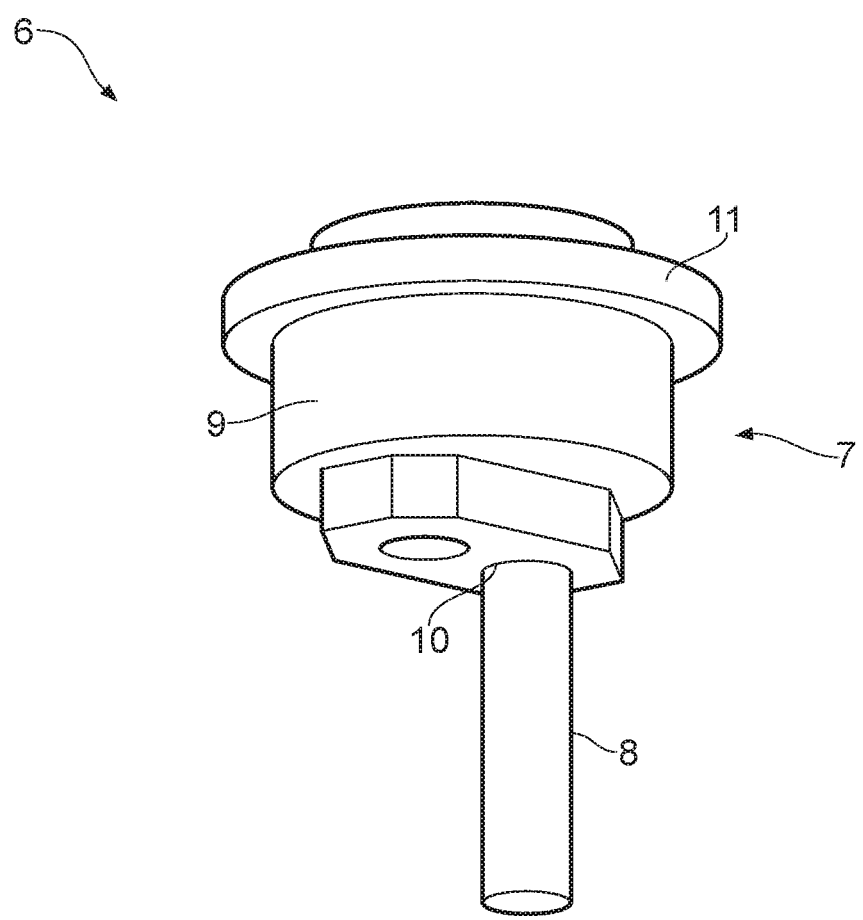
FIG. 5 illustrates an exemplary device (6) of the invention showing one way that the support (7) and the rod (8) can be associated together.

In one embodiment, said support (7) comprises a support body (9) and a rod fixing means (10). In one embodiment said rod fixing means (10) comprises a bore in said support body (9) wherein said bore has cross-sectional dimensions substantially similar to the cross-sectional dimensions of said rod (8) but allowing said rod (8) to be securely contained within said bore. An example of such an embodiment is illustrated in FIG. 5, which shows the rod (8) held in a bore or recess of the support body (9). The rod may be held in place by the forces associated with the sizing of the rod (8) and the bore, i.e. where the cross-sectional dimensions of each are substantially similar with those of the rod (8) being fractionally smaller to allow it to be pushed into the bore and thereafter retained therein. It is also envisaged that the rod might be held in place by means of a fitting such as a snap-lock fitting, or using a suitable adhesive. In an alternative, the support body (9) and rod (8) may be formed together as a single piece, e.g. by injection moulding or similar.

In one embodiment, said support (7) is held in place on the outside of said automated radiosynthesiser (5) by co-operative engagement of a support fixing element (11) and an automated radiosynthesiser fixing element (12). FIG. 5 shows such an embodiment of the device where the support fixing element (11) is a circumferential lip located around the top part of the support (7) that engages with a compatible element on the automated radiosynthesiser. With this embodiment, it is envisaged that the compatible element on the radiosynthesiser will be associated with a mechanism permitting vertical movement of the support (7) so that the rod (8) can be urged towards the reagent vial.

Figure 2:
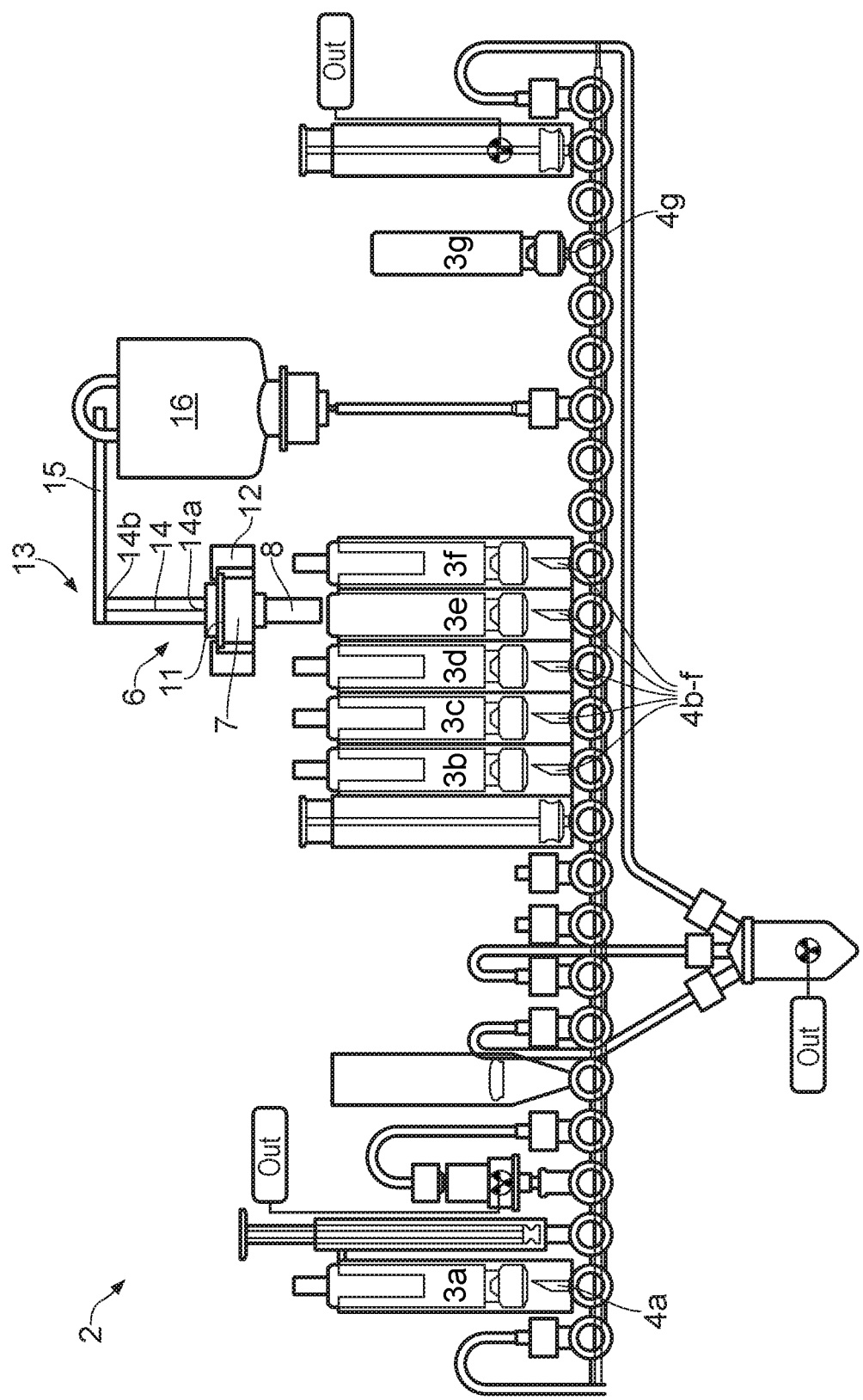
FIG. 2 illustrates a complete FASTlab™ cassette comprising an exemplary device (6) of the invention showing a reagent vial (3e) positioned where the water bottle is positioned in known FASTlab™ cassettes.
Figure 3:
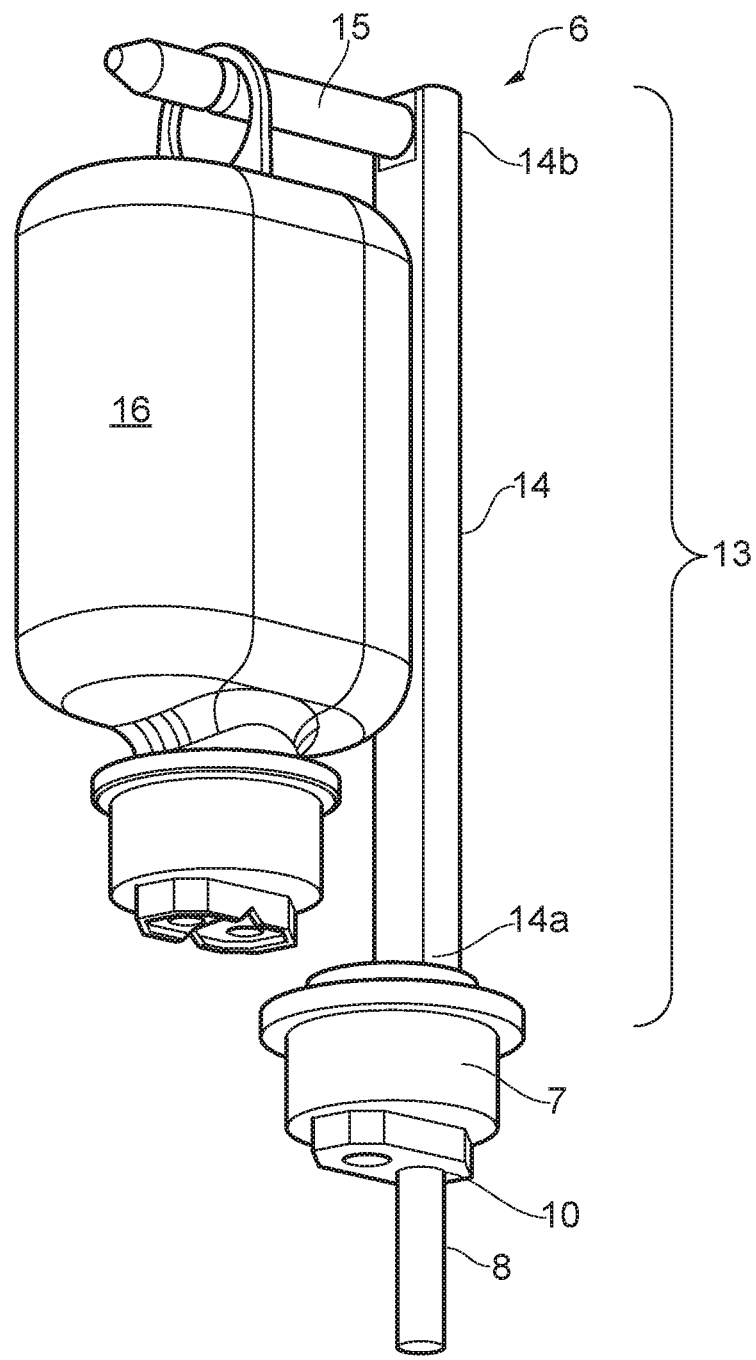
FIG. 3 illustrates an exemplary device (6) of the invention including a water bottle holder (13), with the water bottle (16) shown hanging on the water bottle hanger (15).
Figure 4:
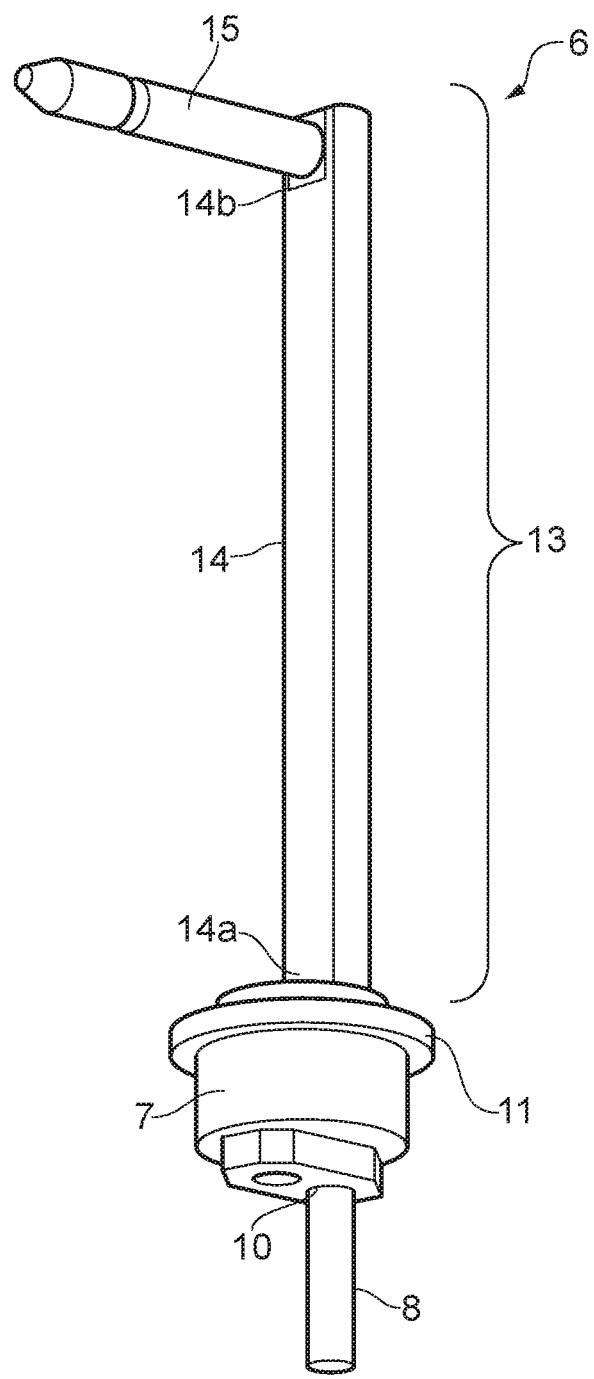
FIG. 4 illustrates the same exemplary device (6) of the invention as illustrated in FIG. 3 without the water bottle present.

In one embodiment of the system of the invention, said device (6) further comprises a water bottle holder (13) housed within said support (7). Examples of this embodiment are illustrated in FIGS. 1-3, where it can be seen that as well as said rod (8), said support (7) also houses a water bottle holder (13). In FIGS. 1-3 this water bottle holder (13) is located diametrically opposite said rod (8).

In one embodiment of the system of the present invention, and as illustrated in FIGS. 1-4, said water bottle holder (13) comprises a rigid spacer (14) having a first end (14a) housed within said support (7) and a second end (14b) comprising a water bottle hanger (15).

Those of skill in the art will recognise that a number of different configurations would achieve the same function as the embodiment illustrated in FIGS. 1-4. It may also be envisaged that the water bottle holder (13) could be present as a separate component to the device (6) and conveniently located elsewhere on the radiosynthesiser, for example on one of the sides of the radiosynthesiser.

In one embodiment of the system of the present invention said radiopharmaceutical is an 18F-labelled radiopharmaceutical. 18F is a positron emitter and radiopharmaceuticals comprising 18F are suitable for imaging using positron-emission tomography (PET).

In one embodiment of the system of the present invention the 18F-labelled radiopharmaceutical is 18F-fluorodeoxyglucose (18F-FDG). The system of the invention is particularly suitable for the synthesis of two batches of 18F-FDG using one cassette, e.g. as described in co-pending patent application PCT/EP2015/076475. A typical 18F-FDG production site produces minimum 2 batches of 18F-FDG in a day, so that a cassette that can only produce 1 batch per day is not ideal. Issues preventing a second run in the same hot cell with a second such 1-batch cassette include residual activity present on the cassette, in the transfer line and the shadow from the waste bottle after completion of the single batch. Therefore for safety reasons back to back runs cannot be carried out on the same apparatus in the same hot cell. This means that in order to produce a second batch of 18F-FDG in the same day using this process, it can be necessary to have a second radiosynthesiser apparatus in a second hot cell. The system of the present invention overcomes these problems by providing additional flexibility in one cassette, which is also a much more cost-effective approach.

A further advantage with the system of the present invention is that it enables a greater range of reagents on one cassette. In one non-limiting example, both ethanol and acetonitrile can be placed in a single cassette for $^{18}$F-FDG synthesis, in contrast to the prior art single-run cassettes that have either ethanol or acetonitrile rather than both, for example the dual-run cassette described in WO2015071288 where only acetonitrile is available. Ethanol can be used in the conditioning of SPE columns, in the cleaning steps between first and second batches, and can be used as a radiostabilizer if desired. Acetonitrile is an ideal drying solvent to remove water effectively during evaporation processes and can also be used in conditioning of SPE columns. Having both solvents available is advantageous therefore in terms of flexibility of the process used.

Non-limiting examples of suitable reagents contained in said reagent vials include ethanol, acetonitrile, deprotecting agent and buffer. In one embodiment said deprotecting agent is selected from HCl, NaOH and $H_3PO_4$. In one embodiment said deprotecting agent is NaOH. In one embodiment said buffer is based on a weak acid, for example selected from citrate, phosphate, acetate and ascorbate. For example where the $^{18}$F-labelled compound of the present invention is $^{18}$F-FDG, the reagent vials include one containing ethanol, one containing acetonitrile, another containing NaOH and another containing a buffer based on a weak acid selected from citrate or phosphate.

In one embodiment of the system of the present invention suitable for production of one or more batches of 18F-FDG said reagents comprise an 18F elution solution, mannose triflate, acetonitrile, ethanol and buffer.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims. All patents and patent applications mentioned in the text are hereby incorporated by reference in their entireties, as if they were individually incorporated.

The invention claimed is:

1. A system for the production of a radiopharmaceutical comprising:
   (i) a cassette comprising all the reagents required to produce two batches of said radiopharmaceutical when a radioisotope is introduced into said cassette, wherein each of said reagents is contained in a stoppered reagent vial that is pierced by a spike by automated movement of said stoppered reagent vial and/or said spike;
   (ii) an automated radiosynthesiser onto which said cassette removably fits and which comprises moving parts that control operation of the cassette, wherein one such moving part is a device to facilitate the automated piercing of one of said stoppered reagent vials wherein said device is attached to the outside of said automated radiosynthesiser and comprises a support and a substantially rigid rod housed within said support, wherein said support comprises a support body and a rod fixing means.

2. The system as defined in claim 1, wherein said rod fixing means comprises a bore in said support body wherein said bore has cross-sectional dimensions substantially similar to the cross-sectional dimensions of said rod but allowing said rod to be securely contained within said bore.

3. The system as defined in claim 1, wherein said support is held in place on the outside of said automated radiosynthesiser by cooperative engagement of a support fixing element and an automated radiosynthesiser fixing element.

4. The system as defined in claim 1, wherein said rod is made from rigid plastic.

5. The system as defined in claim 1, wherein said device further comprises a water bottle holder housed within said support.

6. The system as defined in claim 5, wherein said water bottle holder is located diametrically opposite said rod.

7. The system as defined in claim 5, wherein said water bottle holder comprises a rigid spacer having a first end housed within said support and a second end comprising a water bottle hanger.

8. The system as defined in claim 1, wherein said radiopharmaceutical is an $^{18}$F-labelled radiopharmaceutical.

9. The system as defined in claim 8, wherein said $^{18}$F-labelled radiopharmaceutical is $^{18}$F-fluorodeoxyglucose ($^{18}$F-FDG).

10. The system as defined in claim 9, wherein said reagents comprise an $^{18}$F elution solution, mannose triflate, acetonitrile, ethanol and buffer.

11. A device as defined in the system claim 1.

* * * * *